(12) United States Patent
Czap

(10) Patent No.: US 12,285,455 B2
(45) Date of Patent: *Apr. 29, 2025

(54) CONTROLLED-RELEASE AND STRATIFIED CYCLODEXTRIN INCLUSION COMPLEX VEHICLES

(71) Applicant: CZAP RESEARCH AND DEVELOPMENT, LLC., Napa, CA (US)

(72) Inventor: Al Czap, Napa, CA (US)

(73) Assignee: CZAP RESERACH AND DEVELOPMENT, LLC, Napa, CA (US)

( * ) Notice: Subject to any disclaimer, the term of this patent is extended or adjusted under 35 U.S.C. 154(b) by 176 days.

This patent is subject to a terminal disclaimer.

(21) Appl. No.: 18/184,228

(22) Filed: Mar. 15, 2023

(65) Prior Publication Data
US 2023/0405074 A1    Dec. 21, 2023

Related U.S. Application Data

(60) Division of application No. 17/736,386, filed on May 4, 2022, now Pat. No. 11,633,448, which is a continuation of application No. 16/075,386, filed as application No. PCT/US2017/016583 on Feb. 3, 2017, now abandoned, which is a continuation of application No. 15/232,647, filed on Aug. 9, 2016, now abandoned, and a continuation of application No. 15/285,264, filed on Oct. 4, 2016, now abandoned.

(60) Provisional application No. 62/444,036, filed on Jan. 9, 2017, provisional application No. 62/291,202, filed on Feb. 4, 2016.

(51) Int. Cl.
| | | |
|---|---|---|
| A61K 36/736 | (2006.01) | |
| A61K 31/19 | (2006.01) | |
| A61K 36/185 | (2006.01) | |
| A61K 36/889 | (2006.01) | |
| A61K 38/47 | (2006.01) | |
| A61K 47/69 | (2017.01) | |
| C08B 37/16 | (2006.01) | |
| A61K 9/48 | (2006.01) | |

(52) U.S. Cl.
CPC ............ *A61K 36/736* (2013.01); *A61K 31/19* (2013.01); *A61K 36/185* (2013.01); *A61K 36/889* (2013.01); *A61K 38/47* (2013.01); *A61K 47/6951* (2017.08); *C08B 37/0015* (2013.01); *A61K 9/48* (2013.01); *C12Y 302/01* (2013.01); *C12Y 302/01054* (2013.01)

(58) Field of Classification Search
CPC .... A61K 36/736; A61K 31/19; A61K 36/185; A61K 36/889; A61K 38/47; A61K 47/6951; A61K 9/48; A61K 9/146; A61K 31/352; A61K 31/405; A61K 45/06; A61K 47/40; A61K 31/164; A61K 31/167; A61K 31/198; A61K 47/42; A61K 9/0053; A61K 31/22; C08B 37/0015; C08B 37/0012; C12Y 302/01; C12Y 302/01054; A61P 1/00; A61P 1/04; A61P 1/12; A61P 3/02; A61P 25/00; A61P 25/18; A61P 29/00; A61P 43/00; A61P 39/02; C08L 5/16; C12N 9/1074; A23L 33/175; A23V 2002/00; A23V 2250/5112

See application file for complete search history.

(56) References Cited

U.S. PATENT DOCUMENTS

| | | |
|---|---|---|
| 4,228,160 A | 10/1980 | Szejtli |
| 4,538,920 A | 9/1985 | Drake |
| 4,555,504 A | 11/1985 | Jones |
| 4,869,904 A | 9/1989 | Uekama |
| 5,070,081 A | 12/1991 | Majid |
| 5,134,127 A | 7/1992 | Valentino et al. |
| 5,552,378 A | 9/1996 | Trinh |
| 5,646,131 A | 7/1997 | Badwan |

(Continued)

FOREIGN PATENT DOCUMENTS

| | | |
|---|---|---|
| CN | 1176784 A | 3/1998 |
| EP | 0839528 A1 | 5/1998 |

(Continued)

OTHER PUBLICATIONS

Allen, Effects of oral glutathione supplementation on systemic oxidative stress biomarkers in human volunteers. The journal of alternative and complementary medicine. Sep. 1, 2011;17(9):827-33.

(Continued)

*Primary Examiner* — David Browe
(74) *Attorney, Agent, or Firm* — Kilpatrick Townsend & Stockton LLP

(57) ABSTRACT

The invention provides cyclodextrin inclusion complex delivery vehicles, in which the cyclodextrin inclusion complex comprising acetaminophen and N-acetylcysteine is provided together with enzyme having a cyclodextrin-degrading activity capable of digesting the cyclodextrin, so that upon oral delivery of the vehicle to a target the enzyme is activated and releases acetaminophen and N-acetylcysteine from the cyclodextrin cavity. In alternative aspects, these cyclodextrin inclusion complex delivery vehicles are for example provided in the form of medicaments, food ingredients, medical food ingredients, nutritional supplement ingredients, dietary supplement ingredients, herbicides, insecticides, fungicides, animal repellents, pheromones, plant growth regulators, fragrances, fabrics or packaging materials.

20 Claims, 3 Drawing Sheets

(56) References Cited

U.S. PATENT DOCUMENTS

| | | |
|---|---|---|
| 7,001,893 B2 | 2/2006 | Rao |
| 8,100,295 B2 | 1/2012 | Keller |
| 8,308,340 B2 | 11/2012 | Ferrante |
| 8,499,976 B2 | 8/2013 | Sogaro |
| 8,658,692 B2 | 2/2014 | Kim |
| 8,875,947 B2 | 11/2014 | Obrist |
| 11,633,448 B2 | 4/2023 | Czap |
| 2002/0150616 A1 | 10/2002 | Vandecruys |
| 2004/0235125 A1 | 11/2004 | Kottwitz et al. |
| 2007/0003528 A1 | 1/2007 | Consigny et al. |
| 2008/0161288 A1 | 7/2008 | Boyle et al. |
| 2009/0029020 A1 | 1/2009 | Strassburger |
| 2010/0069536 A1 | 3/2010 | Sau |
| 2011/0014285 A1 | 1/2011 | Herzenberg |
| 2013/0022652 A1 | 1/2013 | Anderson et al. |
| 2013/0251926 A1 | 9/2013 | Wood et al. |
| 2013/0296268 A1 | 11/2013 | Ren et al. |
| 2014/0080812 A1 | 3/2014 | Cloyd et al. |
| 2014/0094433 A1 | 4/2014 | Liu et al. |
| 2014/0315780 A1 | 10/2014 | Badyal et al. |
| 2014/0336149 A1 | 11/2014 | Ren et al. |
| 2015/0150256 A1 | 6/2015 | Wood et al. |
| 2015/0182495 A1 | 7/2015 | Zambelli et al. |
| 2015/0217896 A1 | 8/2015 | Byun et al. |
| 2015/0352155 A1 | 12/2015 | James et al. |
| 2015/0375521 A1 | 12/2015 | Wood et al. |
| 2016/0263245 A1 | 9/2016 | Donovan |
| 2017/0224841 A1 | 8/2017 | Zhang et al. |
| 2017/0224842 A1 | 8/2017 | Czap |

FOREIGN PATENT DOCUMENTS

| | | | |
|---|---|---|---|
| EP | 2 740 475 A1 | 6/2014 | |
| JP | S5944318 A | 3/1984 | |
| JP | 2011-225610 A | 11/2011 | |
| JP | 6884420 B2 | 5/2021 | |
| KR | 2004-0079012 A | 9/2004 | |
| KR | 20120135754 A | 12/2012 | |
| WO | 2000/021842 | 4/2000 | |
| WO | 2002/078627 A2 | 10/2002 | |
| WO | 2007/041266 | 4/2007 | |
| WO | 2017136775 A1 | 8/2017 | |

OTHER PUBLICATIONS

Banasiewicz et al. Microencapsulated sodium butyrate reduces the frequency of abdominal pain in patients with irritable bowel syndrome. Colorectal Disease. Feb. 2012;15(2):204-9.

Banasiewicz et al. Determination of butyric acid dosage based on clinical and experimental studies—a literature review. Gastroenterology Rev 2020;15(2):119-125.

Borycka-Kiciak et al. Butyric acid—a well-known molecule revisited. Przeglad gastroenterologiczny. 2017;12(2):83.

Carneiro et al., Cyclodextrin—drug inclusion complexes: In vivo and in vitro approaches. International journal of molecular sciences. Jan. 2019;20(3):642.

Cavassani, et al. "TLR3 is an endogenous sensor of tissue necrosis during acute inflammatory events." Journal of Experimental Medicine 205, No. 11 (2008): 2609-2621.

Challa, et al. "Cyclodextrins in drug delivery: an updated review." Aaps Pharmscitech 6, No. 2 (2005): E329-E357.

Chaudhary, et al. "Cyclodextrin inclusion complex to enhance solubility of poorly water soluble drugs: A review." International Journal of Pharmaceutical Sciences and Research 4, No. 1 (2013): 68.

Chauncey et al. Comparative enzyme activity of saliva from the sheep, hog, dog, rabbit, rat, and human. Archives of oral biology. Sep. 1, 1963;8(5):615-27.

Chen, et al. "Mechanisms of rhodopsin inactivation in vivo as revealed by a COOH-terminal truncation mutant." Science 267, No. 5196 (1995): 374-377.

Conceicao et al. Cyclodextrins as drug carriers in pharmaceutical technology: the state of the art. Current pharmaceutical design. Apr. 1, 2018;24(13):1405-33.

Cowieson et al. Exogenous microbial amylase in the diets of poultry: what do we know ?. Journal of Applied Poultry Research. Sep. 1, 2019;28(3):556-65.

Davis et al. Cyclodextrin-based pharmaceutics: past, present and future. Nature reviews Drug discovery. Dec. 2004;3(12):1023-35.

Donovan, Joseph D. "Microencapsulation of tributyrin to improve sensory qualities and intestinal delivery." PhD diss., University of Illinois at Urbana-Champaign, 2015.

Dunn, et al. "ARPE-19, a human retinal pigment epithelial cell line with differentiated properties." Experimental eye research 62, No. 2 (1996): 155-170.

Gelb et al., "Complexation of Carboxylic Acids and Anions by Alpha and Beta Cyclodextrins," Journal of Inclusion Phenomen and Molecular Recognition in Chemistry, vol. 7, No. 4, Aug. 1, 1989, 465-476.

Guyenet, "Butyric acid: an ancient controller of metabolism, inflammation and stress resistance?" Whole Health Source [online]; 2009; downloaded from <URL http://wholehealthsource.blogspot.com/2009 /12/butyric-acid-ancient-controller-of.html > on Jun. 2, 2018; 3 pages.

Hamoudi, et al. "Oil-cyclodextrin based beads for oral delivery of poorly-soluble drugs." Current topics in medicinal chemistry 14, No. 4 (2014): 510-517.

Hedges, Allan R. "Industrial applications of cyclodextrins." Chemical reviews 98, No. 5 (1998): 2035-2044.

Hirayama, et al. "Release characteristics of a short-chain fatty acid, n-butyric acid, from its ß-cyclodextrin ester conjugate in rat biological media." Journal of pharmaceutical sciences 89, No. 11 (2000): 1486-1495.

Irie et al. Pharmaceutical applications of cyclodextrins. III. Toxicological issues and safety evaluation. Journal of pharmaceutical sciences. Feb. 1997;86(2):147-62.

Jambhekar, et al. "Cyclodextrins in pharmaceutical formulations I: structure and physicochemical properties, formation of complexes, and types of complex." Drug Discovery Today 21, No. 2 (2016): 356-362.

Klassen, Henry. "Stem cells in clinical trials for treatment of retinal degeneration." Expert opinion on biological therapy 16, No. 1 (2016): 7-14.

Kratsman, et al. "Sodium butyrate attenuates social behavior deficits and modifies the transcription of inhibitory/excitatory genes in the frontal cortex of an autism model." Neuropharmacology 102 (2016): 136-145.

Lukiw, et al. "A2E selectively induces COX-2 in ARPE-19 and human neural cells." Current eye research 31, No. 3 (2006): 259-263.

Ma, et al. "Combining chondroitinase ABC and growth factors promotes the integration of murine retinal progenitor cells transplanted into Rho-/- mice." Molecular vision 17 (2011): 1759.

Manrique Vergara et al. Ácidos grasos de cadena corta (ácido butírico) y patologías intestinales. Nutrición Hospitalaria. 2017;34:58-61.

McMullen et al., Topography of Cyclodextrin Inclusion Complexes, Carbohydrate Research, Pergamon, GB, vol. 31, No. 1, Nov. 1, 1973, 37-46.

Mehta, et al. "ATP-stimulated release of interleukin (IL)-1ß and IL-18 requires priming by lipopolysaccharide and is independent of caspase-1 cleavage." Journal of Biological Chemistry 276, No. 6 (2001): 3820-3826.

Mendel et al. Is the Saliva of the Dog Amylolytically Active ?. Journal of Biological Chemistry. May 1, 1907:3(2):135-43.

Miyagishi, et al. "Prostaglandin E2-induced cell death is mediated by activation of EP2 receptors in motor neuron-like NSC-34 cells." Journal of pharmacological sciences 121, No. 4 (2013): 347-350.

Moran, Digestion and absorption of carbohydrates in fowl and events through perinatal development. The Journal of nutrition. May 1, 1985;115(5):665-74.

Owumi, et al. "Co-administration of N-Acetylcysteine and Acetaminophen Efficiently Blocks Acetaminophen Toxicity." Drug development research 76, No. 5 (2015): 251-258.

(56) References Cited

OTHER PUBLICATIONS

Ricciotti, et al. "Prostaglandins and inflammation." Arteriosclerosis, thrombosis, and vascular biology 31, No. 5 (2011): 986-1000.
Roy, et al. "Host-guest inclusion complexes of α and ß-cyclodextrins with α-amino acids." RSC Advances 4, No. 80 (2014): 42383-42390.
Saenger, et al. "Structures of the common cyclodextrins and their larger analogues beyond the doughnut." Chemical reviews 98, No. 5 (1998): 1787-1802.
Scaffidi, et al. "Release of chromatin protein HMGB1 by necrotic cells triggers inflammation." Nature 418, No. 6894 (2002): 191.
Scarpellini et al. Efficacy of butyrate in the treatment of diarrhoea-predominant irritable bowel syndrome. Digestive and Liver Disease Supplements. Sep. 1, 2007;1(1):19-22.
Sharma, et al. "Development of enteric submicron particles formulation of α-amylase for oral delivery." Pharmaceutical development and technology 18, No. 3 (2013): 560-569.
Simeoli et al. An orally administered butyrate-releasing derivative reduces neutrophil recruitment and inflammation in dextran sulphate sodium-induced murine colitis. British journal of pharmacology. Jun. 2017;174(11):1484-96.
Singh, et al. "Reversal of end-stage retinal degeneration and restoration of visual function by photoreceptor transplantation." Proceedings of the National Academy of Sciences 110, No. 3 (2013): 1101-1106.
Stella, et al. "Cyclodextrins." Toxicologic pathology 36, No. 1 (2008): 30-42.
Stone, et al. "Neural repair and neuroprotection with stem cells in ischemic stroke." Brain sciences 3, No. 2 (2013): 599-614.
Sun, et al. "Recombinant cyclodextrinase from Thermococcus kodakarensis KOD1: expression, purification, and enzymatic characterization." Archaea 2015 (2015).
Takadera, et al. "Prostaglandin E2 induced caspase-dependent apoptosis possibly through activation of EP2 receptors in cultured hippocampal neurons." Neurochemistry international 45, No. 5 (2004): 713-719.
Tovar-Y-Romo, et al. "Endogenous recovery after brain damage: molecular mechanisms that balance neuronal life/death fate." Journal of neurochemistry 136, No. 1 (2016): 13-27.
Uekama, et al. "Recent aspect of cyclodextrin-based drug delivery system." Journal of inclusion phenomena and macrocyclic chemistry 56, No. 1-2 (2006): 3-8.
Wang, et al. "Fragrance-release property of ß-cyclodextrin inclusion compounds and their application in aromatherapy." Journal of Industrial Textiles 34, No. 3 (2005): 157-166.
Wang, et al. "Antibacterial functionalization of wool fabric via immobilizing lysozymes." Bioprocess and biosystems engineering 32, No. 5 (2009): 633-639.
Warre-Cornish, et al. "Migration, integration and maturation of photoreceptor precursors following transplantation in the mouse retina." Stem cells and development 23, No. 9 (2013): 941-954.
West, et al. "Defining the integration capacity of embryonic stem cell-derived photoreceptor precursors." Stem cells 30, No. 7 (2012): 1424-1435.
Wimmer et al., "Cyclodextrins," Ullmann's Encyclopedia of Industrial Chemistry, Jan. 15, 2003, 1-9.
Witschi et al. The systemic availability of oral glutathione. European journal of clinical pharmacology. Dec. 1992;43(6):667-9.
Yanai, et al. "Enhanced functional integration of human photoreceptor precursors into human and rodent retina in an ex vivo retinal explant model system." Tissue Engineering Part A 21, No. 11-12 (2015): 1763-1771.
Yanai, et al. "Differentiation of human embryonic stem cells using size-controlled embryoid bodies and negative cell selection in the production of photoreceptor precursor cells." Tissue Engineering Part C: Methods 19, No. 10 (2013): 755-764.
Lin Shan-Yang et al.: "Inclusion complex formation of acetaminophen by heating and cogrinding with cyclodextrins", Journal of Inclusion Phenomena and Molecular Recognition in Chemistry., vol. 14, No. 2, Jun. 1, 1992 (Jun. 1, 1992), pp. 149-156, XP055940209, NL ISSN: 0923-0750, DOI: 10.1007/BF01029662.
ZAŁęski, et al. "Butyric acid in irritable bowel syndrome." Przeglad gastroenterologiczny 8, No. 6 (2013): 350.
Zhang, et al. "Cyclodextrin-based supramolecular systems for drug delivery: recent progress and future perspective." Advanced drug delivery reviews 65, No. 9 (2013): 1215-1233.
Zhou, et al. "Necroptosis in health and diseases." In Seminars in cell & developmental biology, vol. 35, pp. 14-23. Academic Press, 2014.
Zoppetti, et al. "Water soluble progesterone-hydroxypropyl-ß-cyclodextrin complex for injectable formulations." Journal of Inclusion Phenomena and Macrocyclic Chemistry 57, No. 1-4 (2007): 283-288.
Mehrpour et al., "Why Not Formulate an Acetaminophen Tablet Containing N-Acetylcysteine to Prevent Poisoning?", The Journal of Medical Toxicology, vol. 7, 2011, pp. 95-96.
Mura P, et al., "Ternary systems of naproxen with hydroxypropyl-beta-cyclodextrin and aminoacids", Int J Pharm., 260, pp. 293-302, Jul. 24, 2003.
Szente L, et al., "Fatty Acid-Cyclodextrin Complexes: Properties and Applications", J Incl Phenom Macrocycl Chem., 16, pp. 339-354, Dec. 1, 1993.

CONTROLLED-RELEASE AND STRATIFIED CYCLODEXTRIN INCLUSION COMPLEX VEHICLES

FIELD OF THE INVENTION

The invention is in the field of biochemical constructs for delivery of bioactive agents, including delivery vehicles comprised of molecules carried as inclusions within cyclodextrins that are delivered together with selected enzymes having cyclodextrin-degrading activities.

BACKGROUND OF THE INVENTION

Cyclodextrins are non-reducing cyclic glucose oligosaccharides, frequently the product of cyclomaltodextrin glucanotransferase (E.C. 2.4.1.19; CGTase) catalyzed degradation of starch. Cyclodextrins may have a variety of structures (see Saenger et al., Chem. Rev. 98 (1998) 1787-1802), including three common cyclodextrins with 6, 7 or 8 D-glucopyranonsyl residues ($\alpha$-, $\beta$-, and $\gamma$-cyclodextrin respectively) linked in a ring by $\alpha$-1,4 glycosidic bonds. The frustoconical shape of cyclodextrins forms a cavity or lumen, with the cavities having different diameters depending on the number of glucose units. The scale of selected cyclodextrin (CD) structures is set out in Table 1. Larger cyclodextrins such as cyclomaltononaose ($\delta$-CD) and cyclomaltodecaose ($\epsilon$-CD) are also possible, as well as a variety of cyclodextrin-based supra-molecular structures (see Zhang and Ma, Adv Drug Deliv Rev. 2013 August; 65(9):1215-33).

TABLE 1 cyclodextrin structures

| Cyclodextrin | Lumen diameter (nm) | |
| --- | --- | --- |
| | Inner rim | Outer rim |
| $\alpha$, (glucose)$_6$ | 0.45 | 0.53 |
| $\beta$, (glucose)$_7$ | 0.60 | 0.65 |
| $\gamma$, (glucose)$_8$ | 0.75 | 0.85 |

Cyclodextrins are generally amphipathic, with the wider rim of the lumen displaying the 2- and 3-OH groups and the narrower rim displaying 6-OH. These hydrophilic hydroxyl groups are accordingly on the outside of the lumen, whereas the inner surface is generally hydrophobic and lined with the anomeric oxygen atoms and the C3-H and C5-H hydrogen atoms. In aqueous solution, this hydrophobic lumen may contain water molecules, for example about 3 ($\alpha$-CD), 7 ($\beta$-CD) or 9 ($\gamma$-CD) poorly held but low entropy, and hence relatively easily displaceable water molecules. Thus, otherwise hydrophilic cyclodextrins may bind retain one or more suitably-sized molecules within, or partially within, the lumen of the CD, forming a cyclodextrin inclusion body or complex. For example, non-polar aliphatic and aromatic compounds, including drugs, such as lipophilic drugs, may be bound so as to increase the water solubility of normally hydrophobic compounds or minimize undesirable properties such as odor or taste in certain food additives. For this reason, cyclodextrin inclusions are widely used in the pharmaceutical, food and cosmetic fields (see Hedges, Chem. Rev. 98 (1998) 2035-2044). Cyclodextrins have for example been used in a variety of sustained release drug preparations, such as for inclusion complexes of a medical compound with a hydrophobic cyclodextrin derivative (U.S. Pat. No. 4,869,904).

Cyclodextrins may be chemically modified in a wide variety of ways. For example, to modify the inclusion specificity, physical and chemical properties of the cyclodextrin. Hydroxyl groups of a CD may for example be derivatized. For example, two modified CDs have been used in a number of pharmaceutical products: SBE-$\beta$-CD, or Captisol, a polyanionic variably substituted sulfobutyl ether of $\beta$-CD, and HP-$\beta$-CD, a modified CD commercially developed by Janssen. Additional CD derivatives include sugammadex or Org-25969, in which the 6-hydroxy groups on $\gamma$-CD have been replaced by carboxythio acetate ether linkages, and hydroxybutenyl-$\beta$-CD. Alternative forms of cyclodextrin include: 2,6-Di-O-methyl-$\beta$-CD (DIMEB), 2-hydroxylpropyl-$\beta$-cyclodextrin (HP-$\beta$-CD), randomly methylated-$\beta$-cyclodextrin (RAMEB), sulfobutyl ether $\beta$-cyclodextrin (SBE-$\beta$-CD), and sulfobutylether-$\gamma$-cyclodextrin (SBE$\gamma$CD), sulfobutylated beta-cyclodextrin sodium salt, sulfobutylated beta-cyclodextrin sodium salt, (2-Hydroxypropyl)-alpha-cyclodextrin, (2-Hydroxypropyl)-beta-cyclodextrin, (2-Hydroxypropyl)-gamma-cyclodextrin, DIMEB-50 Heptakis(2,6-di-O-methyl)-beta-cyclodextrin, TRIMEB Heptakis(2,3,6-tri-O-methyl)-beta-cyclodextrin, methyl-beta-cyclodextrin, octakis(6-deoxy-6-iodo)-gamma-cyclodexrin, and, octakis(6-deoxy-6-bromo)-gamma-cyclodexrin. Although CDs such as these have been developed with favorable pharmacological and toxicological profiles, there is the potential that, following administration, residual CDs may perturb the pharmacokinetic properties of drugs, including coadministered drugs, particularly after parenteral administration (see Stella and He, Toxicol Pathol January 2008 vol. 36 no. 1 30-42).

The concern regarding the physiological effect of residual CDs derived from therapeutic CD inclusion complexes follows from the observation that CDs, such as $\alpha$-CD and $\beta$-CD, are resistant to stomach acid and salivary and pancreatic enzyme digestion, and $\gamma$-CD is digested only partly by amylases in the GIT. It is generally accepted that only relatively small amounts of oral CDs are absorbed, and the absorbed CDs are understood to be excreted in the urine without undergoing significant metabolism. Unabsorbed CDs are understood to be fermented by intestinal microbiota.

Cyclodextrins are variably susceptible to enzymatic digestion. For example, $\gamma$-CD is relatively easily hydrolyzed by $\alpha$-amylases whereas $\alpha$-cyclodextrin is more poorly hydrolyzed. CD based therapeutics generally depend on the activity of endogenous amylases to digest the CD. There is however significant variability in amylase activity between patients. For example, patients with pancreatic insufficiency, cystic fibrosis, celiac disease or Crohn's disease, may lack normal amounts of amylase. Similarly, patients, particularly geriatric patients, may be deficient in gastric acid production and thereby fail to create conditions of appropriately low pH in the duodenum to properly trigger release of pancreatic amylase. A similar effect may result from the increasing common use of antacids, histamine-2 blockers, proton pump inhibitors or alternative acid blockers.

A variety of microbial cyclodextrin digesting enzymes have been identified. CD-degrading enzymes include cyclomaltodextrinase (or cyclodextrinase, or CDase, EC 3.2.1.54), maltogenic amylase (EC 3.2.1.133), neopullulanase (EC 3.2.1.135), which have been reported to be capable of hydrolyzing CDs and in some cases additional substrates such as pullulan, and starch. Cyclodextrinase (CDase) catalyzes the hydrolysis of CDs to form linear oligosaccharides of $\alpha$-1,4-linkages, and it can accordingly release substances from CD inclusion complexes. A CDase from Bacillus

*macerans* was reported in 1968, and many CDases from bacteria have since been characterized, such as enzymes from *Bacillus* sp., *Thermoanaerobacter ethanolicus* strain 39E, *Flavobacterium* sp., and *Klebsiella oxytoca* strain M5a1. Archaea CDases have been characterized from *Archaeoglobus fulgidus, Thermococcus* sp. B1001, *Thermococcus* sp. CL1, *Thermofilum pendens*, and *Pyrococcus furiosus*. The structure of the CDase from *Flavobacterium* sp. has been characterized in detail (see Sun et al., Archaea, Volume 2015 (2015), Article ID 397924, reporting the identification of a gene encoding a cyclodextrinase from *Thermococcus kodakarensis* KOD1 (CDase-Tk)).

SUMMARY OF THE INVENTION

Figure 1:
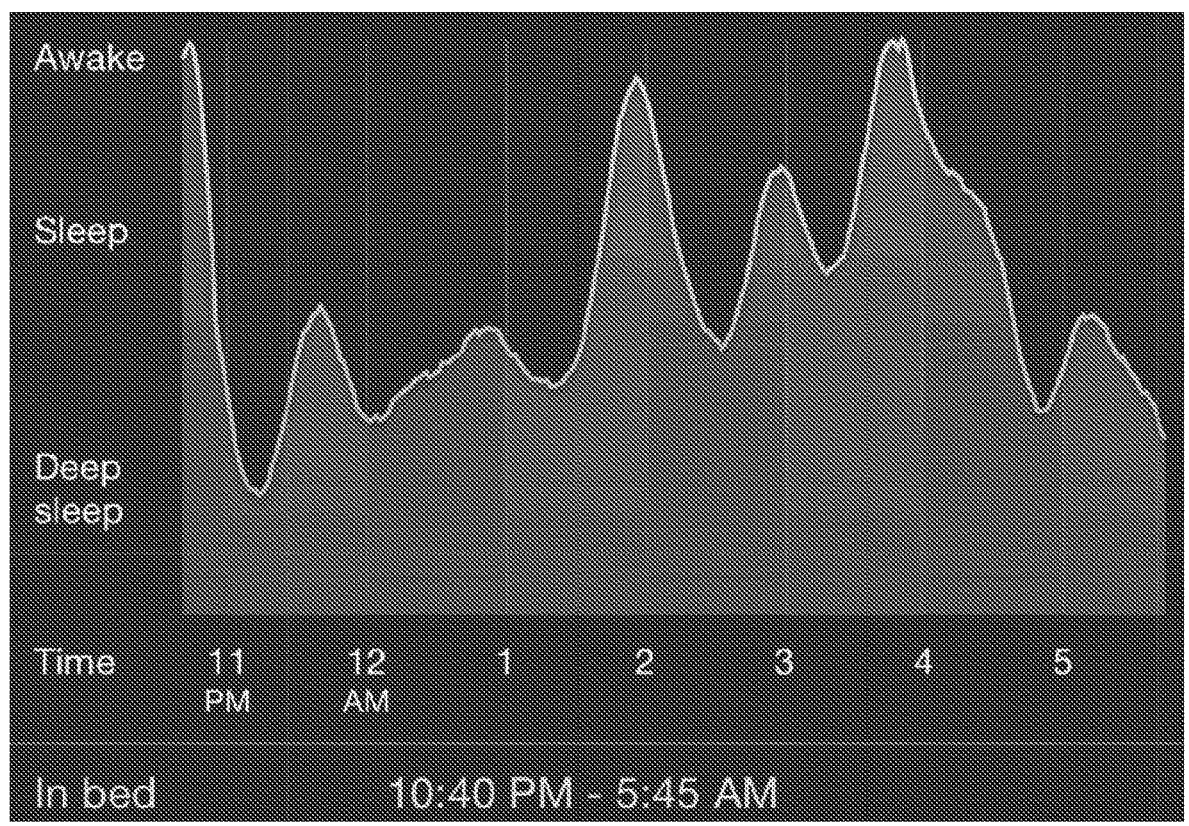
FIG. 1 is a chart illustrating the typical baseline sleep cycle pattern of a subject, based on 912 sleep cycles.

Cyclodextrin inclusion complex delivery vehicles are provided, in which the cyclodextrin has a cavity, with a biologically active molecule that is at least partially retained as a guest molecule within the cavity, forming a cyclodextrin inclusion complex. A biologically acceptable carrier may be provided for the cyclodextrin inclusion complex, so that the guest molecule is stably retained by the cyclodextrin within the biologically acceptable carrier. An enzyme may also be provided in the vehicle, having a cyclodextrin-degrading activity capable of digesting the cyclodextrin retaining the guest molecule. The enzyme may be formulated so that the cyclodextrin-degrading activity is activated on delivery of the vehicle to a target so as to release the guest molecule from the cyclodextrin cavity.

In alternative aspects of the delivery vehicle, the enzyme may be co-formulated with the cyclodextrin inclusion complex or the enzyme may be co-packaged in the delivery vehicle with the cyclodextrin inclusion complex. When the enzyme is co-packaged, the delivery vehicle may further include a biochemically acceptable carrier for the enzyme.

The target may for example be a host organism, such as a human patient, or the target may be an inanimate environment, such as fabric or packaging material.

The enzyme may for example be an amylase, a cyclodextrinase, maltogenic amylase or neopullulanase. An amylase may for example be a mammalian salivary amylase or a pancreatic amylase, or an amylase of fungal, or bacterial origin. A cyclodextrinase may for example be a microbial cyclodextrinase.

The cyclodextrin may for example be a CD derivative, such as a hydrophobic alkylated cyclodextrin or a mixed methylated/ethylated cyclodextrin.

The ratio of the cyclodextrin to the guest molecule may for example be 5:1, 4:1, 3:1, 2:1, 1:1, 1:2, 1:3, 1:4 or 1:5, although a wide range of alternative values for this parameter are also possible, including non-integer ratios.

The cyclodextrin may for example be an alpha, beta or gamma cyclodextrin, although again a very wide range of alternative CD structures may be used.

In select embodiments, the guest molecule may for example be a drug or pro-drug, such as a flavonoid (quercetin), cannabinoid or anti-inflammatory (including acetaminophen). In that circumstance the biologically acceptable carrier may advantageously be a pharmaceutically acceptable carrier. Delivery vehicles of this kind may for example be formulated for delivery by a route that is: parenteral, intravenous, intradermal, subcutaneous, intramuscular, intracranial, intraorbital, ophthalmic, intraventricular, intracapsular, intraspinal, intrathecal, intracisternal, intraperitoneal, intranasal, inhalational, aerosol, topical, intratumoral, sublingual or oral. Similarly, the delivery vehicle may be formulated for sustained release of the drug or pro-drug.

In alternative aspects, the delivery vehicle may include a guest molecule that is a herbicide, insecticide, fungicide, animal repellent, pheromone, or plant growth regulator. In a further alternative, the guest molecule may for example be a fragrance molecule.

In this way, the invention provides alternative embodiments in which CD delivery vehicles may be used as a medicament, as a food ingredient, medical food ingredient, nutritional supplement ingredient, dietary supplement ingredient, a fragrance, as a fabric or packaging, or in an agricultural context as a herbicide, insecticide, fungicide, animal repellent, pheromone, or plant growth regulator.

In various aspects the delivery vehicles accordingly provide a CD inclusion complex together with effective amount of an enzyme having CD-degrading activity, thereby facilitating the release of the guest molecule from the CD in a predictable manner.

In select embodiments, the drug or pro-drug in the delivery vehicle may be a short chain fatty acid or ester derivative thereof, for example butyric (butanoic) acid, propionic acid, acetic acid or ester derivatives thereof, such as a glyceride. Where a glyceride form is provided, a lipase may for example be included in the delivery vehicle. Formulations of this kind may be used for treating gastrointestinal disorders, such as colitis, diverticulitis, Crohn's disease, inflammatory bowel disease, irritable bowel syndrome, inflammation associated with ostomy stoma or granulation associated with ostomy stoma.

Guest molecules may include a variety of amino acids, such as L-phenylalanine, N-acetyl-cysteine (and L-cysteine), L-methionine, L-isoleucine and L-tryptophan. In select embodiments, N-acetyl-cysteine may for example be combined with acetaminophen, for example in a hepatoprotective formulation. Alternative hepatoprotective guest molecules may for example be derived from Silymarin, Curcumin, or TetraHydroCurcumin extracts.

Methods are provided for formulating a cyclodextrin inclusion complex delivery vehicle, comprising: providing a cyclodextrin having a cavity, providing a biologically active molecule that is at least partially retained as a guest molecule within the cavity of the cyclodextrin, forming a cyclodextrin inclusion complex; providing a biologically acceptable carrier for the cyclodextrin inclusion complex, wherein the guest molecule is stably retained by the cyclodextrin within the biologically acceptable carrier; and, optionally, providing an enzyme having a cyclodextrin-degrading activity capable of digesting the cyclodextrin retaining the guest molecule, wherein the enzyme is co-formulated with the cyclodextrin inclusion complex so that the cyclodextrin-degrading activity is activated on delivery of the vehicle to a target so as to release the guest molecule from the cyclodextrin cavity.

Also provided are multicomponent stacked cyclodextrin inclusion complexes, for example comprising: a cyclodextrin having a cavity; an amino acid that is retained as a first guest molecule within the cavity of the cyclodextrin; and, a biologically acceptable lipid that is at least partially retained as a second guest molecule within the cavity of the cyclodextrin. In select embodiments, multicomponent stacked cyclodextrin inclusion complexes may for example includes N-actyl-cysteine (at least partially retained as a first guest molecule within the cavity of the cyclodextrin) and acetaminophen (also at least partially retained as a second guest molecule within the cavity of the cyclodextrin). In these stacked inclusion complexes, the guest molecules may be present in any order, so that where the CD cavity is frustoconical, i.e. having a larger diameter opening and a smaller diameter opening disposed at opposing ends of the cavity, the first guest molecule may be proximal to the smaller opening and the second guest molecule may be proximal to the larger opening (or vice versa).

Methods are provided for treating patients having autism spectrum disorder, involving the administration of an effective amount of a short chain fatty acid cyclodextrin inclusion complex. Similarly, methods of this kind may be used to modulate the microbiome of a patient having a neurological diseases. The short chain fatty acid may for example be butyric acid, and in some embodiments treatment may also include administration of acetic acid (optionally as an inclusion complex).

DETAILED DESCRIPTION OF THE INVENTION

A wide variety of biologically active compounds may be included in delivery vehicles of the invention, for example in the form of pharmaceutical compositions, such as: Docetaxel (US Patent Publications 20140336149, 20130296268); carbamazepine (US Patent Publication 20140080812); Rifampicin (U.S. Pat. No. 7,001,893); cardiac glycosides, particularly digoxin (U.S. Pat. No. 4,555,504); progesterone (see Zoppetti et al., Journal of Inclusion Phenomena and Macrocyclic Chemistry, April 2007, Volume 57, Issue 1, pp 283-288); Albendazole, Mebendazole, Ricobendazole, Fenoprofen, Ketoprofen, Cocaine, Gliclazide, Digitoxin, Macrocyclic compounds (MCCs), ibuproxam, Prochloro-methazine, DY-9760e, NSC-639829, ETH-615, Piroxicam, Levemopamil HCl, Ziprasdone mesylate, Sulindac, Mebendazole, Sulindac, Phenolphthalein, Danazol (see Challa et al., 2005, AAPS PharmSciTech 2005; 6 (2) Article 43); itraconazole, nelfinavirmesylate, telmisartan, 5-fluorouracile and other nucleoside analogues, camptothecin, or flavonoids.

Similarly, in the field of agricultural chemicals, delivery vehicles may be provided that include guest molecules having a wide variety of activities, such as herbicides, insecticides, fungicides, repellents, pheromones, and growth regulators.

Cyclodextrin delivery vehicles of the invention may also include cyclodextrin inclusion complexes with fragrance or other bioactive molecules in a textile or fabric or packaging material (see Wang and Chen, 2005, Journal of Industrial Textiles, Vol. 34, No. 3, 157-166; U.S. Patent Publications: 20150375521, 20150217896, 20150150256, 20140315780, 20130251926). For example, the cyclodextrin digesting enzyme may be incorporated into the textile and the cyclodextrin inclusion complex may be subsequently applied to the enzyme-containing fabric to form the delivery vehicle. Conversely, the CD inclusion complex may be incorporated into the textile, and the enzyme subsequently applied to the textile to form the delivery vehicle. Similarly, both the CD inclusion complex and the enzyme may be incorporated into the textile during manufacture. Enzymes may for example be incorporated into textiles through immobilization involving layered assemblies and/or nanocoatings, with the enzyme attached to the textile substrate so that it retains catalytic activity (analogous for example to processes for antibacterial functionalization of wool by immobilization of lysozymes, as described by Wang et al., 2009, Bioprocess Biosyst Eng 32:633-639, and as reviewed in Advances in Textile Biotechnology, Nierstrasz and Cavaco-Paulo eds., Elsevier, 2010).

In addition to CDs and CD derivatives, a variety of cyclodextrin-based supra-molecular systems are available for delivery of the foregoing range of biologically active molecules (reviewed by Zhang and Ma, Adv Drug Deliv Rev. 2013 August; 65(9):1215-33). Aspects of cyclodextrin-based delivery vehicles accordingly include embodiments that have been characterized as cyclodextrin based nanosponges. These systems may for example be adapted in the context of the present invention for controlled delivery of biologically active molecules, such as drugs.

In select embodiments, the enzyme provided in the vehicle may be formulated so that the cyclodextrin-degrading activity is activated on delivery of the vehicle to a target so as to release the guest molecule from the cyclodextrin cavity. Enzyme activation may for example be accomplished in a medicament, for example for oral delivery, in a dry dosage form, such as a capsule or tablet, in which the enzyme is admixed, so that the enzyme will not be active until activated by moisture in the gastrointestinal tract of a host. Similarly, a wide variety of time release matrices and formulations are known, which may be adapted for use in CD delivery vehicles so as to orchestrate the appropriate activation of the CD-degrading enzyme upon delivery to the target.

In various aspects, CD delivery vehicles may have the enzyme co-formulated with the cyclodextrin inclusion complex, as for example discussed above, or the enzyme may be co-packaged in the delivery vehicle with the cyclodextrin inclusion complex. In the case of co-packaging, the delivery vehicle may for example include a biochemically acceptable carrier for the enzyme—distinct from the carrier for the CD inclusion complex. For example, delivery vehicles may be provided with separated compartments containing the CD inclusion complex and the CD-degrading enzyme, so that the delivery vehicle will be made up of a CD inclusion complex compartment connected to a CD-degrading enzyme compartment. Mechanisms may be provided for the combined release of the CD inclusion complex and the CD-degrading enzyme from the respective compartments in the delivery vehicle. For example, syringes may be provided having distinct compartments of this kind that are discharged by a common discharge mechanism, such as a mechanism that cooperatively displaces pistons in each compartment so as to discharge aliquots of CD inclusion complex and CD-degrading enzyme, so that the enzyme and the complex may then be comingled to activate the enzymatic release of the guest molecule from the CD. Vehicles of this kind may for example be used to dispense a topical cream or other surface-active formulations. A wide variety of delivery vehicles of this kind may be adapted from devices that are known for dispensing two-part compositions such as epoxy resins, two-part medicaments or dental formulations, as for example disclosed in U.S. Pat. Nos. 4,538,920, 8,100,295, 8,308,340, 8,875,947, 8,499,976 and International Patent Publications WO2007041266 and WO2000021842.

There are a wide variety of techniques available to prepare CD inclusion complexes, as for example described in Chaudhary & Patel, IJPSR, 2013; Vol. 4(1): 68-76; US Patent Publication US20090029020; U.S. Pat. Nos. 5,070,081; 5,552,378; and 8,658,692. A common approach is known as the kneading method, which involves mixing CDs with water or an aqueous alcohol to provide a paste. The bioactive molecule may then be added to the paste and kneaded for a specified time. The kneaded mixture may then be dried and passed through sieve if desired. Other known approaches to preparing CD inclusions involve lyophilization, microwave irradiation, and a supercritical fluid antisolvent technique.

The CD delivery vehicles of the invention can be provided alone or in combination with other compounds (for example, nucleic acid molecules, small molecules, peptides, or peptide analogues), in the presence of a carrier, such as a liposome, an adjuvant, or any pharmaceutically or biologically acceptable carrier. Select embodiments include medicaments in a form suitable for administration to animal hosts, such as mammals, for example, humans. As used herein "pharmaceutically acceptable carrier" or "excipient" includes any and all solvents, dispersion media, coatings, antibacterial and antifungal agents, isotonic and absorption delaying agents, and the like that are physiologically compatible. The carrier can be suitable for any appropriate form of administration, including topical, subcutaneous, intradermal, intravenous, parenteral, intraperitoneal, intramuscular, sublingual, inhalational, intratumoral or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the biologically active compound, use thereof in the pharmaceutical compositions of the invention is contemplated. Supplementary active compounds can also be incorporated into the compositions.

Conventional pharmaceutical practice may be employed to provide suitable formulations or compositions to administer the delivery vehicles to subjects. Any appropriate route of administration may be employed, for example, parenteral, intravenous, intradermal, subcutaneous, intramuscular, intracranial, intraorbital, ophthalmic, intraventricular, intracapsular, intraspinal, intrathecal, intracisternal, intraperitoneal, intranasal, inhalational, aerosol, topical, intratumoral, sublingual or oral administration. Therapeutic formulations may be in the form of liquid solutions or suspensions; for oral administration, formulations may be in the form of tablets or capsules; for intranasal formulations, in the form of powders, nasal drops, or aerosols; and for sublingual formulations, in the form of drops, aerosols or tablets.

Cyclodextrin-degrading or digesting enzymes may for example be formulated for oral delivery. Enteric enzyme formulations may for example be provided, such as submicron particle formulations prepared by emulsion solvent evaporation (Sharma et al., Pharm Dev Technol. 2013 May-June; 18(3):560-9). Similarly, delivery vehicles may be formulated as hydrogels (see US Patent Publication 20140094433), or medicated gums (see US Patent Publication 20130022652).

Methods well known in the art for making formulations are found in, for example, "Remington's Pharmaceutical Sciences" (20th edition), ed. A. Gennaro, 2000, Mack Publishing Company, Easton, PA. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of the compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a delivery vehicle of the present invention as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydoxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the biologically active compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the aminocyclohexyl ether compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit.

The biologically active compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability or stability of the compound for the appropriate mode of employment (e.g., oral or parenteral routes of administration).

A composition intended to be administered by injection can be prepared by combining the delivery vehicle of the present invention with water, and preferably buffering agents, so as to form a solution. The water is preferably sterile pyrogen-free water. A surfactant may be added to facilitate the formation of a homogeneous solution or suspension. Surfactants are compounds that non-covalently interact with the aminocyclohexyl ether compound so as to facilitate dissolution or homogeneous suspension of the aminocyclohexyl ether compound in the aqueous delivery system. Surfactants are desirably present in aqueous compositions of the invention because the aminocyclohexyl ether compounds according to the present invention may be hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

The present invention also provides kits that contain a pharmaceutical composition which includes one or more delivery vehicles. The kit also includes instructions for the use of the pharmaceutical. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

An "effective amount" of a CD inclusion complex delivery vehicle according to the invention includes a therapeutically effective amount or a prophylactically effective amount. A "therapeutically effective amount" refers to an amount effective, at dosages and for periods of time necessary, to achieve the desired therapeutic result. A therapeutically effective amount of a delivery vehicle may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the delivery vehicle or active compound are outweighed by the therapeutically beneficial effects. A "prophylactically effective amount" refers to an amount effective, at dosages and for periods of time necessary, to achieve the desired prophylactic result. Typically, a prophylactic dose is used in subjects prior to or at an earlier stage of disease, so that a prophylactically effective amount may be less than a therapeutically effective amount. For any particular subject, the timing and dose of treatments may be adjusted over time (e.g., timing may be daily, every other day, weekly, monthly) according to the individual need and the professional judgment of the person administering or supervising the administration of the compositions.

In select embodiments, the present invention provides a composition or medicament that includes one or more biologically active molecules, selected from biologically active compounds or a solvate, pharmaceutically acceptable salt, ester, amide, complex, chelate, stereoisomer, stereoisomeric mixture, geometric isomer, crystalline or amorphous form, metabolite, metabolic precursor or prodrug thereof, including isolated enantiomeric, diastereomeric and geometric isomers thereof, and mixtures thereof, in combination with a pharmaceutically acceptable carrier, diluent or excipient, and further provides a method for the manufacture of such a composition or medicament.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention. Any priority document(s) and all publications, including but not limited to patents and patent applications, cited in this specification are incorporated herein by reference. All documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual publication were specifically and individually indicated to be incorporated by reference herein and as though fully set forth herein. The invention includes all embodiments and variations substantially as hereinbefore described and with reference to the examples and drawings.

In some embodiments, the invention excludes steps that involve medical or surgical treatment.

EXAMPLES

Example 1: *Serenoa* and *Prunus* Extract

An inclusion complex was made of gamma cyclodextrin (GCD, Wacker Chemi, Germany) with *Serenoa repens* purified seed extract (Indena, Italy) and *Prunus africana* bark extract (Indena, France) in a 2:1 ratio respectively, utilizing the kneading method. The *Serenoa* extract is rich in fatty acids and phytosterols. *Serenoa* extracts may for example include triglycerides and/or free fatty acids such as: oleic acid; lauric acid; caprylic acid; capric acid; tridecanoic acid; myristic acid; pentadecanoic acid; palmitic acid; palmitoleic acid; heptadecanoic acid; stearic acid; vaccenic acid; linoleic acid; linolenic acid; arachidic acid; gondoic acid; behenic acid; lignoceric acid. Phytosterols in *Serenoa* extracts may for example include: campesterol, β-sitosterol; and stigmasterol. Similarly, the *Prunus* extract includes a wide variety of such compounds, which may for example include: N-butylbenzenesulfonamide, atraric acid, β-sitosterol, β-sitostenone, and fatty acids such as linoleic, palmitic, oleic, stearic, linolenic, lauric, and myristic acids, docosanol, behenic acid, ursolic acid, lignoceric acid, ferulic acid and friedelin.

*Serenoa* extract oil is amber in color while *Prunus* extract resembles "tar balls" comprising an almost black, hardened extract that can be kneaded by hand. Both extracts have an almost pleasant deep fruit odor, which disappears almost entirely when included in the cyclodextrin inclusion complex.

After drying and grinding, samples of the inclusion complex were assayed for susceptibility to enzymatic release of the herbal extracts. In this assay, 1 gram of the inclusion complex was mixed into 20 ml of distilled water in Vessel 1 and an equal amount of 1 gram inclusion complex and 20 ml of distilled water, along with 20 mg of undiluted amylase powder (Enzyme Development Corporation, New York) was mixed in Vessel 2. Both vessels were heated to 37° C. with stirring every 5 minutes.

At the 20-minute point of the assay, color change started to become evident in Vessel 2 and was quite prominent at the 30-minute point. In contrast, in Vessel 1, without the addition of the enzyme, an off white color was maintained (consistent throughout 5 more hours). The contents of Vessel 2 became markedly darker as the amylase digested the GCD inclusion complex. After 30 minutes, Vessel 2 was revealing some of the native color of the extracts as the protective envelope of the GCD was broken down by the enzyme, allowing the raw ingredients to become visible again. In addition, after 30 minutes, in Vessel 2 but not Vessel 1, the odor of the two ingredients again became apparent. At 30 minutes, there was no separation of ingredients in Vessel 1, as evidenced by the lack of any lipid presence, with the contents of the vessel remaining as flecks of inclusion complex. However, in Vessel 2 at 30 minutes, the breakdown of the inclusion complex was evident not only in the body of the solution, but by a ring of *Serenoa* and *Prunus* extracts that, as lipid substances, create an oily slick around the vessel—with droplets of the oils visible on the white ceramic surface of Vessel 2.

This example illustrates the effective release of fatty acids and phytosterols from plant extracts formulated as CD inclusion complexes. This embodiment is accordingly exemplary of inclusion complexes that comprise one or more fatty acids and/or phytosterols such as: oleic acid; lauric acid; caprylic acid; capric acid; tridecanoic acid; myristic acid; pentadecanoic acid; palmitic acid; palmitoleic acid; heptadecanoic acid; stearic acid; vaccenic acid; linoleic acid; linolenic acid; arachidic acid; gondoic acid; behenic acid; lignoceric acid; campesterol, β-sitosterol; stigmasterol; N-butylbenzenesulfonamide, atraric acid, β-sitostenone, docosanol, behenic acid, ursolic acid, lignoceric acid, ferulic acid and friedelin.

Example 2: Butyric Acid

An inclusion complex was made of alpha cyclodextrin (ACD, Wacker Chemi, Germany) with butyric acid (Vigon, USA), utilizing the kneading method. Butyric acid is a fatty acid (also known as butanoic acid), which at room temperature is a clear, lightweight oil which has an unpleasant, somewhat rancid odor that disappears almost entirely when included in a cyclodextrin inclusion complex. Butyric acid odor can be detected by the human nose in concentrations above 10 ppm, and can be irritating to the skin, eyes and respiratory system.

After drying and grinding, samples of the inclusion complex were assayed for susceptibility to enzymatic release of butyric acid. In this assay, 1 gram of the inclusion complex was mixed into 20 ml of distilled water in Vessel 1 and an equal amount of 1 gram inclusion complex and 20 ml of distilled water, along with 20 mg of undiluted amylase powder (Enzyme Development Corporation, New York) was mixed in Vessel 2. Both vessels were heated to 37° C. with stirring every 5 minutes.

At the 25-minute point butyric acid odor started to become evident in Vessel 2, and became yet more prominent at the 35-minute point. In contrast, Vessel 1, without the addition of the enzyme, maintained the same faint odor without increase for 5 more hours.

Example 3: Hemp Oil Extract

An inclusion complex was made of gamma cyclodextrin (GCD, Wacker Chemi, Germany) with purified hemp oil extract (CV Sciences, USA), utilizing the kneading method. Hemp oil typically contains a variety of fatty acids, phytosterols and physiologically active ingredients, such as: linoleic acid, α-linolenic acid, oleic acid, β-sitosterol, campesterol, phytol, cycloartenol, γ-tocopherol and cannabidiol, as well as a small percentage of terpene-like substances, labelled for reference herein, "Hemp Essential Oils" as discussed below.

After drying and grinding, samples of the inclusion complex were assayed for susceptibility to in vivo enzymatic release of the hemp oil extract. In this assay, 390 mg of the inclusion complex was encapsulated in size 0 capsules. A second set of capsules was prepared, containing 390 mg of the inclusion complex along with 10 mg of undiluted amylase powder (Enzyme Development Corporation, New York).

A 43 year-old male subject, in good health, with 912 nights of sleep cycle recording was given 2 capsules of each preparation on different days 30 minutes before his standard bedtime of 11 p.m., well after his evening meal, with no food to induce salivary amylase.

Figure 2:
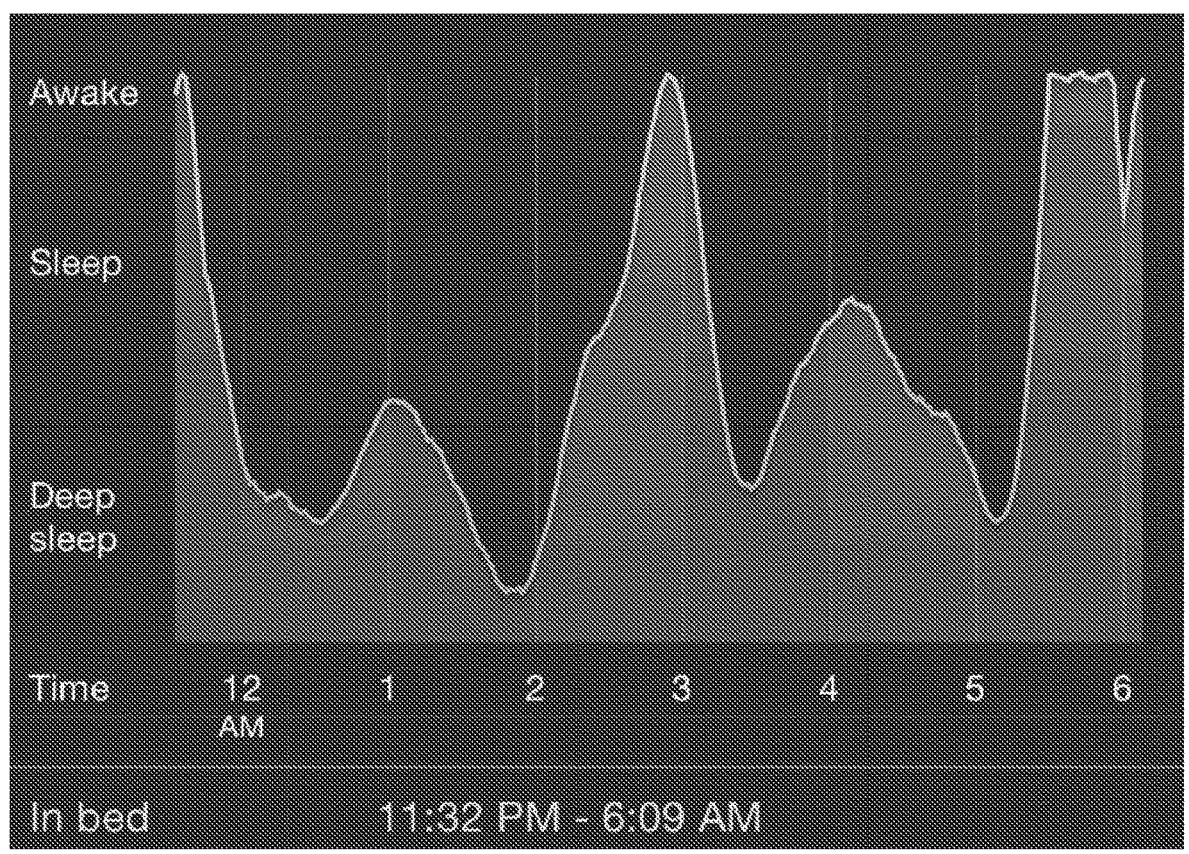
FIG. 2 is a chart illustrating the sleep cycle of the subject, following administration of a hemp oil cyclodextrin inclusion complex formulation without amylase, showing significantly less deep sleep that the sleep pattern of the subject following administration of the hemp oil cyclodextrin inclusion complex formulation with amylase.
Figure 3:
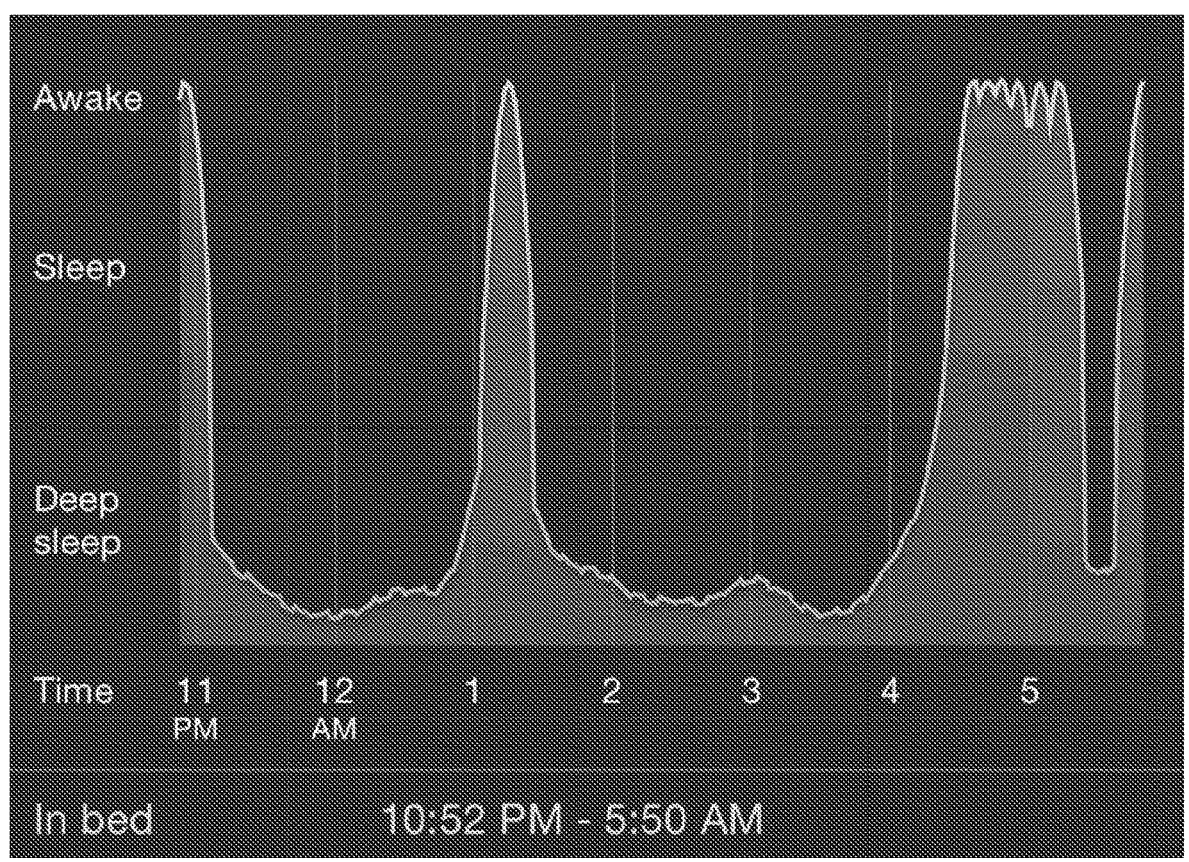
FIG. 3 is a chart illustrating the sleep cycle of the subject, following administration of a hemp oil cyclodextrin inclusion complex formulation with amylase, showing a dramatically deeper sleep pattern than the baseline sleep cycle pattern of the subject.

FIG. 1 shows the typical sleep pattern of the subject with duration and level of deep sleep. FIG. 2 shows the sleep pattern after taking the inclusion complex without any addition of amylase, illustrating a sleep pattern that shows slightly more deep sleep than the typical baseline, with the subject reporting an average sleep in his rating. FIG. 3 dramatically demonstrates what the subject described as "his most restful sleep in years". Except for arising to use the bathroom briefly, with a quick return to sleep, the entire sleep pattern reaches a previously unachieved sleep depth and deep sleep time.

This Example illustrates the in vivo release of physiologically active ingredients from an inclusion complex utilizing an amylase added to the inclusion complex formulation. An aspect of this Example is the independence of the formulation from any reliance on salivary or digestive amylase to release the active ingredients.

In exemplary embodiments, alternative formulations may include a variety of biologically active molecules derived from hemp or *cannabis* plants, for example cyclodextrin inclusion complexes of various cannabinoids, such as cannabigerol (CBG), cannabichromene (CBC), tetrahydrocannabivarin (THCV), tetrahydrocannabinol (THC), cannabidiol (CBD), and cannabinol (CBN).

Example 4: Glaucoma

The subject in this Example is a California Medical Doctor with experience utilizing medical marijuana since 1996. The subject self administered capsules prepared as described in Example 3, containing 390 mg of the hemp oil inclusion complex with 10 mg of amylase powder. After several days of sequential use, the subject had noticeable improvement in his glaucoma, with these results from use of the inclusion complex being better than any combination of isolated cannabidiol or standardized product that the subject had utilized in the past.

Example 5: Stratified Inclusion Complexes

This Example relates to the production of CD inclusion complex mixtures, in which a plurality of alternative guest molecules form inclusion complexes with a plurality of alternative cyclodextrins, with each of the guest molecules matched in size and/or affinity to a corresponding cyclodextrin having a cavity sized or adapted to stably retain the guest molecule. In this way, a complex mixture of distinct, for example differently-sized, biologically active molecules may be formulated as a stratified inclusion complex mixture.

In an exemplified embodiment, Hemp Essential Oil, (see Table 2 for ratio by percent) was sequentially formulated with alpha and beta cyclodextrins. A sample of, Hemp Essential Oil, was first added to a slurry of alpha cyclodextrin and water, with kneading over time to form inclusion complexes of guest molecules sized to fit within the cavity of alpha cyclodextrin. Next, a cyclodextrin having a larger cavity, beta cyclodextrin, was added over time with additional water and kneading to complete the size stratified inclusion complex mixture by forming inclusion complexes of guest molecules too large to fit within the cavity of alpha cyclodextrins. By first forming the inclusion complexes with a cyclodextrin having a smaller cavity, and then forming the inclusion complexes with a cyclodextrin having a larger cavity, this process provides an inclusion complex mixture in which guest molecules are housed in the cyclodextrin with which they form the most stable inclusion complex, avoiding the suboptimal capture of small molecules by the larger CD. This process may be iterative, with a succession of larger or differently modified CDs used to form complex stratified inclusion complexes in which the guest molecules are successively retained in chemically or sterically matched cyclodextrins.

TABLE 2

Hemp Essential Oil Analysis

| Compound | Content % |
| --- | --- |
| ALPHA THUJENE | 0.09 |
| ALPHA PINENE | 7.6 |
| CAMPHENE | 0.12 |
| OCTEN 1 OL 3 | 0.02 |
| SABINENE | 0.09 |
| BETA PINENE | 3.03 |
| MYRCENE | 31.1 |
| ALPHA PHELLANDRENE | 0.24 |
| DELTA-3-CARENE | 0.78 |
| ALPHA TERPINENE | 0.17 |
| PARACYMENE | 0.17 |
| LIMONENE | 0.95 |
| EUCALYPTOL | 0.72 |
| BETA PHELLANDRENE | 0.26 |
| OCIMENE CIS BETA | 1.13 |
| OCIMENE TRANS BETA | 10.21 |
| GAMMA TERPINENE | 0.19 |
| TRANS 4 THUYANOL | 0.06 |
| PARA ALPHA DIMETHYL STYRENE | 0.13 |
| TERPINOLENE | 8.9 |
| CIS EPOXY OCIMENE | 0.06 |
| EPOXY TERPINOLENE | 0.33 |
| PARACYMENE 8 OL | 0.43 |
| TERPINENE 4 OL | 0.06 |
| ALPHA TERPINEOL | 0.03 |
| HEXYLE BUTYRATE | 0.07 |
| TRANS ANETHOL | 0.14 |
| HEXYLE HEXANOATE | 0.1 |
| ALPHA YLANGENE | 0.03 |
| ALPHA COPAENE | 0.04 |
| BETA BOURBONENE | 0.04 |
| ISOCARYOPHYLLENE | 0.19 |
| CIS ALPHA BERGAMOTENE | 0.21 |
| BETA CARYOPHYLLENE | 13.69 |
| TRANS ALPHA BERGAMOTENE | 1.3 |
| ALPHA GUAIENE | 0.12 |
| TRANS BETA FARNESENE | 1.72 |
| ALPHA HUMULENE | 4.47 |
| ALLO-AROMADENDRENE | 0.43 |
| GAMMA MUUROLENE | 0.14 |
| BETA SELINENE | 0.95 |
| ALPHA SELINENE | 0.69 |
| ALPHA MUUROLENE | 0.23 |
| BETA BISABOLENE | 0.37 |
| GAMMA CADINENE | 0.07 |
| 7 EPI-ALPHA SELINENE | 0.35 |
| BETA SESQUIPHELLENDRENE+ DELTA CADINENE | 0.09 |
| GAMMA SELINENE | 0.5 |
| SELINA-3,7(11)-DIENE | 0.44 |
| NEROLIDOL | 0.1 |
| GERMACRENE B | 0.1 |
| SPATHULENOL | 0.21 |

TABLE 2-continued

Hemp Essential Oil Analysis

| Compound | Content % |
| --- | --- |
| OXYDE DE CARYOPHYLLENE | 2.21 |
| EPOXYDE HUMULENE | 0.65 |
| CARYOPHYLLANE 4(12), 8(13)DIENE 5-BETA-OL | 0.1 |
| TOTAL % | 96.62 |

Synthetic mixtures of stratified inclusion complexes may be formulated so as to provide an altered ratio of biologically active molecules compared to an initial mixture from which the inclusion complexes are made. To take the exemplified embodiment described above, the alpha cyclodextrin inclusion complexes from a series of, Hemp Essential Oil, samples may be pooled, and then to this pooled alpha cyclodextrin formulation a single aliquot of beta cyclodextrin inclusion complex may be added, to provide a formulation that is enriched in smaller biologically active molecules, in the form of inclusion complexes, compared to the composition of the original, Hemp Essential Oil. Alternatively, as described above, the synthetic mixture of stratified inclusion complexes may be produced so as to recapitulate the relative abundance of biologically active molecules in a selected starting material. In the exemplified embodiment, this was achieved by using a 4:1 ratio of alpha cyclodextrin to beta cyclodextrin, reflecting the fact that approximately 80% of the, Hemp Essential Oil, sample was made up of biologically active molecules sized to fit within alpha cyclodextrin, with bulk of the remaining 20% sized to fit within beta cyclodextrin inclusion complexes.

In exemplary embodiments, synthetic mixtures of stratified inclusion complexes are provided that contain adjusted ratios of cannabinoids and terpenes, for example derived from *Cannabis* or hemp samples or extracts. These mixtures may contain inclusion complexes of various cannabinoids, such as cannabigerol (CBG), cannabichromene (CBC), tetrahydrocannabivarin (THCV), tetrahydrocannabinol (THC), cannabidiol (CBD), and cannabinol (CBN). Terpenes (isoprenoids) in these mixtures may for example include: a-pinene, ocimene, caryophyllene (β-caryophyllene), camphene, camphor, eucatyptol, humulene (α-humulene), myrcene, g-terpinene, cis-nerolidol, carene, terpinolene, terpineol, trans-nerolidol, cymene (p-cymene), linalool, phellandrene, guaiol, limonene, isopulegol, cary-oxide, a-terpinene, geraniol, valencene, fenchol, borneol (isoborneol), phytol, sabinene, menthol, cedrene, nerolidol, isopulegol, geranyl acetate, pulegone and bisabolol.

Stratified inclusion complexes may be formulated for delivery with one or more enzymes having cyclodextrin-degrading activities capable of digesting the cyclodextrins retaining the guest molecules. In select embodiments, enzymes may for example be selected that have preferential or exclusive activity on a subset of the cyclodextrins found in the mixture. In this way, the stratified cyclodextrin inclusion complex delivery vehicle may be adapted so that there are two or more distinct enzymes, and the distinct enzymes are formulated to have distinct cyclodextrin-degrading activities that are activated on delivery of the vehicle to two or more distinct targets, for example two distinct portions of the gastrointestinal tract.

Example 6: Short Chain Fatty Acid Inclusion Complexes

This Example relates to drugs, dietary supplements, foods or medical food preparations comprising an inclusion complex of individual or combined short chain fatty acids (SCFA), with a hydrophobic or hydrophilic cyclodextrin (including alpha, beta or gamma CDs, and modified CDs such as ethylated CDs). The SCFA may be present in the form of an ester, such as a glyceride (mono-, di- or triglyceride), a salt or another pharmaceutically acceptable derivative. The SCFA inclusion complex may be provided in a dosage form with an enzyme having a cyclodextrin-degrading activity capable of digesting the CD retaining the SCFA guest molecule, such as an alpha, beta or gamma amylase(s). Similarly, a lipase may be added to the formulation to release SCFAs from lipids, for example to act on an ester of the SCFA such as a glyceride. These formulations may be prepared as an immediate release dosage or food form, or a sustained release dosage or food form. In sustained release dosage forms, the dissolution and release of one or more of the components may be sustained or retarded at a controlled rate, including the SCFA medical ingredient, the CD and/or the amylase. For example, the amylase, with or without the CD inclusion compound, may be formulated in the form of coated beadlets or granules in a wide range of sustained release coatings or resin forms. Similarly, particularly if a lipase is included in the formulation, a glyceride, such as a triglyceride, may be provided on a matrix, for example spray dried on a cellulose matrix, for example in admixture with the lipase. These formulations may for example be adapted to control or maintain the blood concentration of a medical compound or a metabolite thereof, such as the SCFA, at an effective level for a longer period of time than would be the case in the absence of the sustained release carrier.

An aspect of these formulations is the use of a dosage form that provides the SCFA to the small and large intestine of a subject, such as a human or mammal. The formulations may for example be used for adjunctive or therapeutic purposes in the treatment of a gastrointestinal disorder, such as colitis, diverticulitis, Crohn's disease, inflammatory bowel disease, or irritable bowel syndrome (IBS). In another aspect, these formulations may be used to provide prophylactic or therapeutic treatments of neoplastic diseases of the gastrointestinal tract, such as colon cancer. In a further aspect, these formulations may be used to provide prophylactic or therapeutic treatments of insulin sensitivity in diabetics. In a further aspect, these formulations may be used to provide prophylactic or therapeutic treatments that improve thermogenic activity with subsequent weight loss.

In select embodiments, these formulations provide a drug preparation, which comprises an inclusion complex composed of at least one SCFA, as the active ingredient, capable of being complexed as an inclusion compound with at least one hydrophobic cyclodextrin. In particular embodiments, the SCFA may for example be one or more of butyric (butanoic) acid, propionic acid, or acetic acid. Multiple SCFAs may for example be provided in select rations, for example from 9:1 to 1:9. Select SCFAs may for example be formulated in an optimized formulation, for example comprising 75-95% butyric acid, 1-20% propionic acid, and 1-10% acetic acid, for example approximately 85% butyric, 10% propionic, and 5% acetic acid.

Example 7: Gastrointestinal Therapy with Butyric Acid Formulation

This Example relates to treatment of generalized gastrointestinal dysfunction. A 48 year-old woman with active and longstanding symptoms of clinically diverse gastrointestinal dysfunction was given 30-milligram capsules of a butyric acid inclusion complex, prepared as described in Example 2, 4 capsules twice daily. Three weeks after initiating treatment, her physician reported clinically relevant evidence of therapeutic efficacy, and that for the first time in 4 years the patient exhibited what would be characterized as normal GI function.

Example 8: Gastrointestinal Therapy with SCFA Formulation

This Example illustrates treatment of specific gastrointestinal symptoms with a formulation comprising a mixture of SCFAs. The subject presented as a 65 year-old man with intermittent liquid diarrhea, with predictable symptomatic flaring after morning coffee (especially with morning citrus), or after eating a rich evening meal. Treatment was initiated with an SCFA inclusion complex medication, with capsules comprising butyric acid (27 milligrams), propionic acid (2.5 milligrams) and acetic acid (2.5 milligrams) in an inclusion complex with alpha cyclodextrin. The initial treatment regimen was 4 capsules, 3 times daily. This was later lowered to twice daily. Within 24 hours of first dosing, liquid diarrhea ceased, and did not recur during the entire 5 week period of treatment. During treatment, the patient reported that stools became completely consistent, and the volume of fecal discharge decreased dramatically. The patient was also able to discontinue what had been a regular antacid treatment after meals and before bedtime, and reported improved tolerance of moderate alcohol intake.

Example 9: IBD Therapy with Butyric Acid Formulation

This Example illustrates alleviation of symptoms of chronic irritable bowel disease (IBD). The patient presented as a 52 year-old woman with chronic IBD of 30 years, undergoing symptomatic treatment with loperamide in 2 to 4 doses daily. Treatment was initiated with the butyric acid formulation of Example 2, 3 capsules 2 times daily commencing during an IBD flare up with no concomitant loperamide treatment during 7 days of treatment with the butyric acid inclusion complex formulation. Within 48 hours, all diarrhea ceased. The patient also reported distinct appetite suppression after 7 days of treatment. This Example accordingly demonstrates therapeutic efficacy in the treatment of IBD, as well as the use of an SCFA inclusion complex formulation as an appetite suppressant.

Example 10: Ostomy Inflammation

This example illustrates the treatment of symptoms associated with an ostomy, including inflammation and granulation. This is a case history of a medical doctor with a history of three-year recurrent ostomy inflammation and infection. Prior to treatment with a butyrate CD formulation, the clinical history of the patient was as follows:
  Colectomy in 1971 for Ulcerative Colitis;
  Ongoing, unknowing exposure to Stachybotrys November 2012-January 2014;
  Immune system dysfunction secondary to Stachybotrys exposure;
  From January 13-June 15, recurrent bouts of pouchitis, and an enterocutaneous fistula, neither of which responded to multiple doses of ciprofloxacin and metronidazole; 5 laparotomies in that time, to mitigate damage; ultimately take down of an intestinal reservoir replaced with a standard Brooke Ileostomy;

Two surgeries to debride and ultimately move ileostomy due to non-healing skin wound;

Persistent granulation tissue around stoma, did not respond to two steroid injections administered in conjunction with tacrolimus cream.

Treatment was initiated with an oral butyric acid formulation prepared in accordance with Example 2, 8 capsules twice per day. Capsules were 30 milligrams net butyric acid in a sustained release CD formulation with amylase enzyme. Healing of inflammation was progressive to verge of resolution when treatment ceased. Within 1 week of cessation of butyrate CD therapy, the lesion began breaking down and growing again. The lesion worsened for a total of 2 weeks. Upon re-initiation of butyric acid CD treatment, began to heal again Example 11: Myelofibrosis This example illustrates the treatment of symptoms associated with myelofibrosis. A patient suffering from myelofibrosis was treated with a quercetin CD formulation. The formulation was prepared from a powder of quercetin (Glanbia Nutritionals) formed as an inclusion complex with gamma cyclodextrin, dried and mixed with amylase powder. At the initiation of quercetin CD treatment, the patient was in need of blood transfusions approximately every 10 days. Following initiation of the quercetin CD treatment, the patient was able to go 20 days between transfusions. The supervising physician, whose practice has utilized quercetin since 1984, stated that the patient did not get this result after a regimen of standard quercetin supplementation.

This example illustrates that delivery vehicles of the invention may be used so as to provide advantageous delivery of flavonoids, including bioflavonoids such as quercetin.

Example 12: Autism

This Example includes three case histories of treatment of autism spectrum disorder (ASD) in children, using a butyric acid alpha-cyclodextrin inclusion complex compounded with amylase.

A five year old male, O, with confirmed diagnosis of ASD was treated with an oral butyric acid alpha-cyclodextrin inclusion complex, prepared utilizing the kneading method, compounded with amylase. Dosing was 30 milligrams net butyric acid twice daily. Within 10 days, a psychiatric assessment noted dramatic improvement in ASD symptoms. This was in keeping with caregivers' assessment of much improved quality of life.

A six year old male, M, with confirmed diagnosis in the autism spectrum was treated daily with ¼ tsp of a butyric acid alpha-cyclodextrin inclusion complex, prepared utilizing the kneading method, compounded with amylase enzyme. M had previously generally been unable to make eye contact when speaking to someone, even his mother, and was unable to tie his shoes. Twenty-two hours after initiation of butyrate CD therapy, following two doses, M tied his shoes and made direct eye contact with his mother when expressing pride in his achievement.

A 17 year old female with confirmed diagnosis in the autism non-verbal spectrum was treated with 3 capsules twice daily of a butyric acid alpha-cyclodextrin inclusion complex, prepared utilizing the kneading method, compounded with amylase enzyme, net 180 mg butyrate. Within 3 days the patient displayed better eye contact, became calm, and can now, unsolicited, point and identify animals and pictures in a picture book, even verbalizing the names of particular characters.

Autism has been associated with a variety of gastrointestinal symptoms, and studies have found evidence of distinct characteristics of the gut microbiome in autistic patients, with related evidence of beneficial effects of butyrate. Accordingly, in one aspect, the present invention provides butyric acid cyclodextrin inclusion complex formulations for use so as to modulate the gut microbiome of patients with neurological disease.

Example 13: Hypoallergenic Meal Replacement and Elemental Diet Formulations

This Example relates to the production of CD inclusion complex mixtures, in which individual amino acids, or groups of amino acids form inclusion complexes with cyclodextrin(s), for example so as to mask taste and improve solubility of the less soluble amino acids.

In an exemplified embodiment, CD inclusion complexes may be formed from individual amino acids that are known to be bitter or sulfur dominant in taste, such as: L-Phenylalanine, N Acetyl-Cysteine (and L Cysteine), L-Methionine, L-Isoleucine and L-Tryptophan. In one example, these amino acids were each individually included in beta cyclodextrin, in an equimolar ratio, utilizing the kneading method. A second group was included utilizing the kneading method, in an equimolar ratio, in gamma cyclodextrin. The material was then dried and ground. Upon addition to tap water, it was found that these inclusions were completely soluble and masked the objectionable taste extremely well compared to the base material.

In another embodiment, the same amino acids (L-Phenylalanine, N Acetyl-Cysteine (and L-Cysteine), L-Methionine, L-Isoleucine and L-Tryptophan) were premixed as a group and then included utilizing the kneading method, in an equimolar ratio, in beta cyclodextrin. A second group was included utilizing the kneading method, in an equimolar ratio, in gamma cyclodextrin. The materials were then dried and ground. Upon addition to tap water, it was also found that these inclusions as a combination were completely soluble and masked the objectionable taste extremely well.

These methods may accordingly be utilized for naturally occurring or synthetic amino acids, individually or in combination. Beta cyclodextrin inclusions may in some circumstances have restricted dosing requirements, for example being limited to a relatively small amount daily by oral administration. Accordingly, for formulations that are intended for dosing in small quantities of specific amino acids, beta cyclodextrin may be an appropriate choice for inclusion (which may be advantageous from a cost perspective compared to alpha or gamma cyclodextrins). Alternatively, where size permits, amino acids may be included in an alpha cyclodextrin inclusion complex.

Commercial meal replacements are available for use in gastrointestinal practice, such as Vivonex™ Plus, a prepackaged product of amino acids, soybean oil (for necessary fat), maltodextrin/cornstarch (carbohydrate source) and basic vitamins and minerals with preservatives. The five amino acids having bitter or sulfur dominant in taste (L-Phenylalanine, N Acetyl-Cysteine (and L Cysteine), L-Methionine, L-Isoleucine and L-Tryptophan) may be perceived to make products of this kind unpalatable. Ingredients in products of this kind, and corresponding products of the invention that include one or more amino acids present in the form of a CD inclusion complex, may for example include:

maltodextrin (from corn), L-glutamine, modified cornstarch, L-leucine, L-arginine acetate, soybean oil and less than 2% of magnesium gluconate, L-lysine acetate, calcium glycerophosphate, L-isoleucine, L-valine, L-phenylalanine, sodium citrate, L-threonine, potassium citrate, L-cysteine hydrochloride, citric acid, L-methionine, L-tyrosine, L-histidine hydrochloride, L-aspartic acid, L-proline, L-tryptophan, disodium phosphate, potassium chloride, choline bitartrate, L-serine, L-alanine, glycine, ascorbic acid, polyglycerol esters of fatty acids, taurine, L-carnitine, alpha-tocopheryl acetate, zinc sulfate, potassium sorbate and bha and bht and tocopherols (to maintain freshness), ferrous sulfate, niacinamide, vitamin a palmitate, calcium pantothenate, copper gluconate, vitamin D3, pyridoxine hydrochloride, manganese sulfate, riboflavin, thiamine hydrochloride, folic acid, chromium chloride, biotin, potassium iodide, sodium molybdate, sodium selenite, phytonadione, vitamin B12.

These meal replacement and elemental diet formulations may for example be formulated so as to provide, in a serving size of approximately 79.4 grams: Protein (As Amino Acids) 13.5 g; Fat 2 g; Carbohydrate 57 g; Vitamins, minerals and other ingredients 6.9 g.

Meal replacement formulations may alternatively provide an amino acid ratio modeled on a natural protein source, such as the egg.

In one exemplary embodiment, canola oil, a source of fatty acids, was included in a gamma cyclodextrin inclusion complex, in an equimolar ratio, utilizing the kneading method. The material was then dried and ground as a premix to add to a meal replacement. The amount for one serving of the included premix was, in grams: Canola Oil 2.0; Carbohydrate from Gamma Cyclodextrin 10.5. In this embodiment, the amino acids L-Phenylalanine, N Acetyl-Cysteine, L-Methionine, L-Isoleucine and L-Tryptophan were premixed as a group and then included in gamma cyclodextrin, in an equimolar ratio, utilizing the kneading method. The material was then dried and ground as a premix to add to a meal replacement. The ratio for one serving of the included premix was, in grams:
Amino Acids:

| | |
|---|---|
| L-Phenylalanine | 0.85 |
| N Acetyl-Cysteine | 0.5 |
| L-Methionine | 0.5 |
| L-Isoleucine | 0.85 |
| L-Tryptophan | 0.42 |

Carbohydrate from Gamma Cyclodextrin . . . 26.8

This material was then added to the following amino acid amounts in grams:

| | |
|---|---|
| L-Leucine | 2.2 |
| L-Arginine | 2.1 |
| L-Valine | 1.0 |
| L-Tyrosine | 0.5 |
| L-Histidine | 0.5 |
| L-Lysine | 0.76 |
| L-Threonine | 0.6 |
| L-Aspartic | 0.5 |
| L-Glutamine | 3.2 |
| L-Proline | 0.5 |
| L-Serine | 0.85 |
| L-Alanine | 0.85 |
| Glycine | 0.85 |
| Taurine | 0.34 |
| L-Carnitine | 0.34 |

The total weight of amino acids present in the blend is 18.21 grams. The total weight of Gamma Cyclodextrin in the blend is 37.3 grams. The total weight of Canola Oil in the blend is 2 grams.

A dry blend of this material was made and the following was added:

| | |
|---|---|
| Rice maltodextrin | 19.7 grams |
| Sodium Chloride | 366 milligrams |

Formulations may include a wide variety of vitamins and minerals. For example a multi vitamin mineral premix containing highly absorbable, biologically active ingredients, total approximately 3 grams, may be added, and may include:

Vitamin A (2.00 IU from Beta Carotene and 1,000 IU as Palmitate) 3,000 IU.
Vitamin C (as Ascorbic Acid) 50 mg.
Vitamin D (as Vitamin D3) 200 IU.
Vitamin E (as d-Alpha Tocopheryl) 40 IU.
Thiamin (as Thiamin HCl) 5 mg.
Riboflavin (as Riboflavin 5'-Phosphate Sodium) 2 mg.
Niacin (20 mg as Niacinamide and 5 mg as Niacin) 25 mg.
Vitamin B6 (as Pyridoxal 5'-Phosphate) 2 mg.
Folate (200 mcg as L-5-Methyltetrahydrofolate from L-5-Methyltetrahydrofolic Acid, Glucosamine Salt) 200 mcg.
Vitamin B12 (10 mcg as Adenosylcobalamin and 10 mcg as Methylcobalamin) 20 mcg.
Biotin 100 mcg.
Pantothenic Acid (as Calcium Pantothenate) 20 mg.
Choline (as Citrate) 100 mg.
Calcium (120 mg as Calcium Citrate and 90 mg as Calcium Malate) 210 mg.
Iron (as Iron Picolinate) 3 mg.
Iodine (as Potassium Iodide) 225 mcg.
Magnesium (60 mg as Magnesium Citrate and 30 mg as Magnesium Malate) 90 mg.
Zinc (as Zinc Picolinate) 3 mg.
Selenium (as L-Selenomethionine) 40 mcg.
Copper (as Copper Picolinate) 0.3 mg.
Manganese (as Manganese Picolinate) 3 mg.
Chromium (Chromium Nicotinate Glycinate Chelate)*40 mcg.
Molybdenum (as Molybdenum Picolinate) 20 mcg.
Potassium (30 mg as Potassium Citrate and 30 mg as Potassium Malate) 60 mg.
Boron (as Boron Picolinate) 0.5 mg.
Vanadium (as Vanadium Picolinate) 20 mcg.

In accordance with the foregoing embodiment, a total serving size is provided of approximately 80 grams. This produced a palatable, hypoallergenic, Vivonex-style meal replacement, without the characteristic intolerable taste of bitter or sulfur amino acid residual. Alternative serving sizes, ingredients and ratios of ingredients are also provided. Additional or alternative ingredients may for example include nicotinamide riboside, butyric acid, and acetic Acid.

In another embodiment, the amino acids L-phenylalanine and L-tryptophan were individually included in a gamma cyclodextrin inclusion complex, in an equimolar ratio, utilizing the kneading method. Each material was then dried and ground to add to a premix to further add to a meal replacement. Another variation of this was repeated with the two amino acids premixed and then included, with the same end result. Subsequently, the individual amino acids N acetyl-cysteine, L-methionine, and L-isoleucine were each included in a gamma cyclodextrin inclusion complex, in an equimolar ratio, utilizing the kneading method. An oil may also be provided in the final product, for example so as to occupy less space in the final formula. For purposes of this example, canola oil was added to each amino acid inclusion by kneading in the same amount of oil as amino acid in each individual process. L-Phenylalanine was formulated with the addition of 0.85 grams canola oil, N acetyl-cysteine was formulated with the addition of 0.5 grams canola oil, and L-methionine was formulated with the addition of 0.5 gram canola oil. Surprisingly, the oil when added in these quantities was evidently incorporated into the gamma cyclodextrin inclusion complex. Accordingly, not only does the cyclodextrin admit the amino acid into the cavity, masking offensive taste of the amino acid, but the CD also admits at least a portion of the canola triglyceride, locking the amino acid in the CD, with the lipid forming a notional plug in the CD cavity. The invention accordingly provides formulations of this kind that provide a soluble, flavor masked amino acid with in combination with a lipid. This example was repeated with an individual fatty acid, capric acid, instead of the canola oil, with the same surprising result. This results in a stacked, double inclusion complex within a single cyclodextrin. Each of the Canola treated materials were then dried and ground to add to a premix to further add to a meal replacement. Another variation of this was repeated with these same three amino acids premixed and then included, with subsequent addition of Canola Oil, with the same end result.

As set out above, this Example relates to elemental diet formulations, with CDs for palatability (with and without enzymes to facilitate the breakdown the CD). In that context, there is some evidence that in some patients an elemental diet may cause a reduction in pancreatic enzyme secretion, and for patients for whom this is true, the use of one or more enzymes in the present formulations may be particularly advantageous.

Amino acid supplements may also be provided as CD inclusion complexes, with and without enzymes to facilitate the breakdown the CD. This may for example be particularly advantageous for branch chain amino acids, such as leucine, isoleucine and valine. Accordingly, in the present example, leucine and valine have been formulated in a palatable alpha CD inclusion complex, and Isoleucine has been formulated in a palatable gamma CD inclusion complex.

Example 14: Acetaminophen Inclusion Complexes

In one aspect, this Example relates to the production of CD inclusion complex mixtures, in which anti-inflammatories or pain relieving substances form inclusion complexes with cyclodextrin(s) to mask taste and improve solubility as standalone inclusions. In alternative embodiments, other substances may be included in the inclusion compounds. These embodiments may be formulated with and without one or more enzymes to facilitate the breakdown the CD.

In an exemplified embodiment, acetaminophen was included in an alpha cyclodextrin inclusion complex, in an equimolar ratio, utilizing the kneading method. A second amount was included utilizing the kneading method, in an equimolar ratio, in beta cyclodextrin. A third amount was included utilizing the kneading method, in an equimolar ratio, in gamma cyclodextrin. Each material was then dried and ground. Upon addition to tap water, it was found that these inclusions were completely soluble and masked the objectionable taste quite well.

In a further embodiment, N-acetyl-cysteine, as in Example 13, above, was included utilizing the kneading method, in an equimolar ratio, in gamma cyclodextrin. The material was then dried and ground. Upon addition to tap water, it was found that the inclusion was completely soluble and greatly masked the usual objectionable taste and smell.

An admixture was then made of the acetaminophen/gamma-cyclodextrin and N-acetyl-cysteine/gamma cyclodextrin dried powders. When mixed with tap water, it provided a therapeutic dose of acetaminophen while providing the hepatoprotective function of the N-acetyl-cysteine. The combination of the two ingredients, as inclusions, provides a vehicle that more readily delivers the acetaminophen due to enhanced solubility, but provides also a delivery form for N-acetyl-cysteine with dramatically less odor and objectionable taste. Formulations of this kind may for example be augmented with minor additions of flavor and sweetener compounds, for example as a powder dosage form or incorporated into other standard dosage forms such as capsules or tablets, including sustained release forms, with and without enzymes to facilitate the breakdown the CD.

Example 15: Hepatoprotective Formulations

This Example relates to the production of CD inclusion complex mixture(s), in which hepatoprotective substance(s) form inclusion complexes with cyclodextrin(s), for example so as to mask taste and improve solubility, as stand alone inclusions or when added to other substances that may also be inclusion compounds.

In an exemplified embodiment, N-acetyl-cysteine, as in Example 13, was included utilizing the kneading method, in an equimolar ratio, in gamma cyclodextrin. The material was then dried and ground. Upon addition to tap water, it was found that the inclusion was completely soluble and masked the objectionable taste quite well.

Silymarin extract (Indena SPA) was included utilizing the kneading method, in an equimolar ratio, in gamma cyclodextrin. The material was then dried and ground. Upon addition to tap water, it was found that the inclusion was completely soluble and masked the objectionable taste extremely well.

Curcumin extract (Sabinsa) was included utilizing the kneading method, in an equimolar ratio, in gamma cyclodextrin. The material was then dried and ground. Upon addition to tap water, it was found that the inclusion was completely soluble and masked the objectionable taste extremely well.

Curcumin extract (Sabinsa) was included utilizing the kneading method, in a 1:2 molar ratio, in gamma cyclodextrin. The material was then dried and ground. Upon addition to tap water, it was found that the inclusion was completely soluble and masked the objectionable taste extremely well.

TetraHydroCurcumin (*Sabina*) was included utilizing the kneading method, in an equimolar ratio, in gamma cyclodextrin. The material was then dried and ground. Upon addition to tap water, it was found that the inclusion was completely soluble and masked the objectionable taste extremely well.

TetraHydroCurcumin (*Sabina*) was included utilizing the kneading method, in a 1:2 molar ratio, in gamma cyclodextrin. The material was then dried and ground. Upon addition to tap water, it was found that the inclusion was completely soluble and masked the objectionable taste extremely well.

N-acetyl-cysteine, for example under the trade name Mucomyst, is given in emergency room situations for acetaminophen overdose, for example for patients with risk for hepatotoxicity according to the Rumack-Matthew nomogram of toxicity levels. Most ER utilization is currently by an intravenous route, due to the extremely unpleasant taste and odor of N-acetyl-cysteine. Accordingly, an embodiment provides a mixture of included N-acetyl-cysteine, with or without a CD degrading enzyme such as an amylase, for example formulated for administration with water or juice to patients as a rescue remedy for acetaminophen poisoning. Such formulations may alternatively be provided as a prophylactic, for example in conjunction with every day or high dose acetaminophen usage. Similarly, additional hepatoprotective agents may be provided, including silymarin, curcuminoids, and other known hepatoprotective agents, including, but not limited to, grapefruit, naringin, naringenin, blueberries, cranberries, flavonoids, catechins, epicatechins, anthocyanidins, proanthocyanidins, resveratrol, cactus pear, chamomile, *spirulina*, propolis, and Beta-glucans.

In an alternative aspect, acetaminophen itself may be formulated with an amino acid CD inclusion complex, with and without enzymes to facilitate the breakdown the CD. For example, an N-acetyl-cysteine CD inclusion may be formulated, particularly for use as a pediatric formulation, so as to prevent hepatic injury. In alternative embodiments, the acetaminophen may for example be included in the same CD as the N-actyl-cysteine, for example with the acetaminophen as the initial inclusion and the amino acid as the secondary inclusion, or vice versa, in alternative forms of a stacked multicomponent inclusion complex. In select embodiments, utilizing gamma cyclodextrin, both acetaminophen and N-actyl-cysteine may be included within the CD cavity.

The combination of two or more ingredients, as inclusions, provides a vehicle that more readily delivers the ingredients due to enhanced solubility, and provides a delivery form with vastly less odor and objectionable taste that may easily be adjusted with minor addition of flavor and sweetener as a powder dosage form or incorporated into other standard dosage forms such as capsule, or tablet, including sustained release forms.

Example 16: Stacked Inclusion Complexes

This Example relates to the production of CD inclusion complex mixture(s), in which substance(s) form inclusion complexes with cyclodextrin(s) to mask taste and improve solubility as stacked inclusions. In an exemplified embodiment, N-acetyl-cysteine, as in Example 13, was included utilizing the kneading method, in an equimolar ratio, in gamma cyclodextrin. Acetaminophen, in an equimolar ratio, was added to the N-acetyl-cysteine inclusion forming a stacked inclusion. The material was then dried and ground. Upon addition to tap water, it was found that the inclusion was completely soluble and masked the objectionable taste quite well. In select embodiments, stacked inclusion complexes may be formulated so as to facilitate the inclusion of multiple compounds into a single cyclodextrin, for example so as to reduce product dosage volume.

The invention claimed is:

1. A method for treating pain and/or inflammation and ameliorating toxicity caused by acetaminophen usage and/or overdose, comprising orally administering to a human subject in need thereof an effective amount of a composition comprising:
a cyclodextrin having a cavity;
N-acetylcysteine and acetaminophen retained as stacked guest molecules within the cavity of the cyclodextrin, forming a cyclodextrin inclusion complex;
a pharmaceutically acceptable carrier for oral delivery of the cyclodextrin inclusion complex, wherein the N-acetylcysteine and acetaminophen are retained in the cyclodextrin inclusion complex within the pharmaceutically acceptable carrier; and, an enzyme having a cyclodextrin-degrading activity capable of digesting the cyclodextrin retaining the N-acetylcysteine and acetaminophen, wherein the cyclodextrin-degrading activity is activated on oral delivery of the composition to a human subject so as to release the N-acetylcysteine and acetaminophen from the cyclodextrin cavity.

2. The method of claim 1, wherein the enzyme is an amylase, a cyclodextrinase, or neopullulanase.

3. The method of claim 2, wherein the enzyme is an amylase.

4. The method of claim 2, wherein the amylase is a maltogenic amylase.

5. The method of claim 2, wherein the amylase is a mammalian salivary amylase, a mammalian pancreatic amylase or a microbial amylase.

6. The method of claim 5, wherein the microbial amylase is a bacterial amylase.

7. The method of claim 1, wherein the cyclodextrin is an alpha-cyclodextrin, a beta-cyclodextrin, or a gamma-cyclodextrin.

8. The method of claim 1, wherein the cyclodextrin is a beta-cyclodextrin.

9. The method of claim 6, wherein the cyclodextrin is a beta-cyclodextrin.

10. The method of claim 1, wherein the cyclodextrin is a hydrophobic alkylated cyclodextrin or a mixed methylated/ethylated cyclodextrin.

11. The method of claim 1, wherein the composition is formulated for sustained release of the N-acetylcysteine and acetaminophen.

12. The method of claim 9, wherein the composition is formulated for sustained release of the N-acetylcysteine and acetaminophen.

13. A method of formulating a composition for oral delivery to a human subject in need thereof, the method comprising:
providing a cyclodextrin having a cavity, wherein the cyclodextrin is an alpha-cyclodextrin, a beta-cyclodextrin, or a gamma-cyclodextrin;
admixing the cyclodextrin with N-acetylcysteine and acetaminophen so that N-acetylcysteine and acetaminophen are retained as stacked guest molecules within the cavity of the cyclodextrin, forming a cyclodextrin inclusion complex;
admixing the cyclodextrin inclusion complex with a pharmaceutically acceptable carrier for oral delivery, wherein the N-acetylcysteine and acetaminophen are retained by the cyclodextrin inclusion complex within the pharmaceutically acceptable carrier; and,
admixing an enzyme with the cyclodextrin inclusion complex and the pharmaceutically acceptable carrier, the enzyme having a cyclodextrin-degrading activity capable of digesting the cyclodextrin retaining the cyclodextrin inclusion complex, wherein the cyclodextrin-degrading activity is activated on oral delivery of the composition to a human subject so as to release the N-acetylcysteine and acetaminophen from the cyclodextrin cavity.

14. The method of claim 13, wherein the enzyme is an amylase, a cyclodextrinase, or neopullulanase.

15. The method of claim 13, wherein the enzyme is an amylase.

16. The method of claim 15, wherein the amylase is a maltogenic amylase.

17. The method of claim 15, wherein the amylase is a mammalian salivary amylase, a mammalian pancreatic amylase or a microbial amylase.

18. The method of claim 17, wherein the microbial amylase is a bacterial amylase.

19. The method of claim 13, wherein the cyclodextrin is a beta-cyclodextrin or a gamma-cyclodextrin.

20. The method of claim 18, wherein the cyclodextrin is a beta-cyclodextrin.

* * * * *